United States Patent
Rosenthal

[11] Patent Number: 6,064,896
[45] Date of Patent: May 16, 2000

[54] NON-INVASIVE MEASUREMENT OF BLOOD GLUCOSE USING INSTRUMENTS THAT HAVE LESS PRECISE DETECTION CAPABILITY

[75] Inventor: Robert D. Rosenthal, Gaithersburg, Md.

[73] Assignee: Futrex Inc., Gaithersburg, Md.

[21] Appl. No.: 09/073,941

[22] Filed: May 6, 1998

[51] Int. Cl.$^7$ ...................................................... A61B 5/00
[52] U.S. Cl. .......................................... 600/316; 600/322
[58] Field of Search ..................................... 600/300, 310, 600/316, 318, 319, 322, 365; 128/920, 921; 356/39

[56] References Cited

U.S. PATENT DOCUMENTS

5,840,020  11/1998  Heinonen et al. ....................... 128/920

*Primary Examiner*—Eric F. Winakur
*Attorney, Agent, or Firm*—Rothwell, Figg, Ernst & Kurz

[57] ABSTRACT

A method and apparatus are disclosed for improving an accuracy characteristic of a quantitative measurement instrument for measuring a blood analyte concentration by using lower precision sensor devices. One embodiment of the method includes calculating a correction factor based on an elapsed time from a last meal and a substantially typical rise and fall pattern of blood analyte concentrations in the bloodstream. The correction factor is part of a regression analysis equation employed by the blood analyte measurement instrument. A second embodiment includes a method whereby a series of indicator variables are allocated based on the elapsed time from a last meal, and uses the indicator variables in a regression analysis equation. An apparatus having an introducer means for introducing an energy into blood present in a body part of a subject, a detector for detecting the energy emerging from the body part, with the detector producing an electrical signal indicative of the emerging energy, an input element for entering a time from a last meal of the subject, a storage element for storing a regression equation and a correction factor, and a processor for using the regression equation and the correction factor to yield a predicted value of the blood analyte concentration.

32 Claims, 10 Drawing Sheets

NON-INVASIVE MEASUREMENT OF BLOOD GLUCOSE USING INSTRUMENTS THAT HAVE LESS PRECISE DETECTION CAPABILITY

BACKGROUND OF THE INVENTION

1. Field of the Invention

The present invention relates to instruments and methods for the non-invasive quantitative measurement of blood analytes. More specifically, this invention relates to a new and improved method of increasing an accuracy characteristic for a quantitative measurement instrument, allowing the quantitative measurement instrument to have a less precise detection capability.

2. Description of Background Art

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

Persons that have diabetes have a common characteristic in that their bodies have difficulty maintaining reasonable blood glucose levels during various times of the day. In order to allow for survival and avoid long-term complications, most persons with diabetes take medication in an attempt to keep their blood glucose at a reasonably constant level.

The variation in blood glucose levels is a function of many different parameters, such as eating habits, medication, stress, exercise level, etc. The two most common causes of variations in blood glucose levels in persons with diabetes are meals and diabetes medication.

Several methods exist for measuring blood glucose levels. One method is to obtain a blood sample from the patient. The blood sample is placed on a chemically treated carrier and is inserted into an instrument. The instrument analyzes the blood sample and provides a blood glucose level reading in a short period of time. However, the blood sample method has drawbacks, including the painful and invasive nature of the test, which provides an avenue for infection.

An alternative measurement method is the near-infrared quantitative analysis instrument which non-invasively measures blood analytes. Non-invasive quantitative measurement instruments are generally known. See U.S. Pat. Nos. 5,086,229; 5,028,787; 5,077,476; 5,218,207; and 5,703,364. Non-invasive measurement is ideal for persons who must regularly monitor their blood glucose. The non-invasive blood glucose measurement instrument analyzes near-infrared energy following interactance with venous or arterial blood, or transmission through a blood-containing body part. These instruments give accurate blood glucose level readings and readily lend themselves to at-home testing by diabetics. Typically, the measurement is performed on a finger of the subject.

A limitation of the near-infrared blood glucose measurement instruments has been that near-infrared quantitative measurement instruments must be highly precise in their measurement capabilities. Since the amount of glucose in the body is less than one thousandth of the total constituents, variations of the constituents which exist among different people has in the past made highly precise instruments necessary in order to obtain an accurate measurement.

In addition to the near-infrared technology, there are other technologies that have promise for measurement of blood glucose, such as radio-frequency technology. Such devices are less expensive than near-infrared quantitative measurement devices, however, radio-frequency measurement devices do not provide reasonable precision and are therefore lacking.

Thus, there is a need for accurate non-invasive measurement of blood analytes when using technology that does not provide precise direct measurement.

SUMMARY OF THE INVENTION

In accordance with the present invention, a method is disclosed for improving the accuracy characteristic of a quantitative measurement instrument for the measurement of a blood analyte concentration when using less precise sensor instrumentation. The method according to the first embodiment of the present invention comprises adding a correction factor to the regression analysis equation. The regression analysis equation is used by the quantitative measurement instrument to obtain a predicted level of the blood analyte concentration. The correction factor uses the elapsed time from a last meal and the general blood analyte trend to produce a correction factor based on the elapsed time.

In another embodiment of the present invention, a second form of regression analysis equation having indicator variables is used by the quantitative measurement instrument to obtain a predicted level of the blood analyte concentration. The second embodiment employs nine indicator variables, allocated on the basis of the time elapsed since the last meal and the general blood analyte trend.

In yet another embodiment of the present invention, division derivative math is employed in the regression analysis equation to obtain a predicted level of the blood analyte. One or two division derivative terms may be used, based on the linearity of the blood analyte level concentration.

In yet another embodiment, a quantitative measurement instrument for non-invasive measurement of a blood analyte concentration is given, comprising an introducing means including an energy source for introducing an energy into blood present in a body part of a subject, a detector circuit means for detecting the energy emerging from the body part, with the detector circuit means producing a first electrical signal indicative of the emerging energy, an input means for entering a time since a last meal of the subject, a storage means for storing a correction factor, and a processing means for processing the first electrical signal by using a regression equation and the correction factor to yield a predicted value of the blood analyte concentration, with the correction factor increasing an accuracy characteristic of the quantitative measurement instrument.

DETAILED DESCRIPTION OF THE PREFERRED EMBODIMENTS

Figure 1:
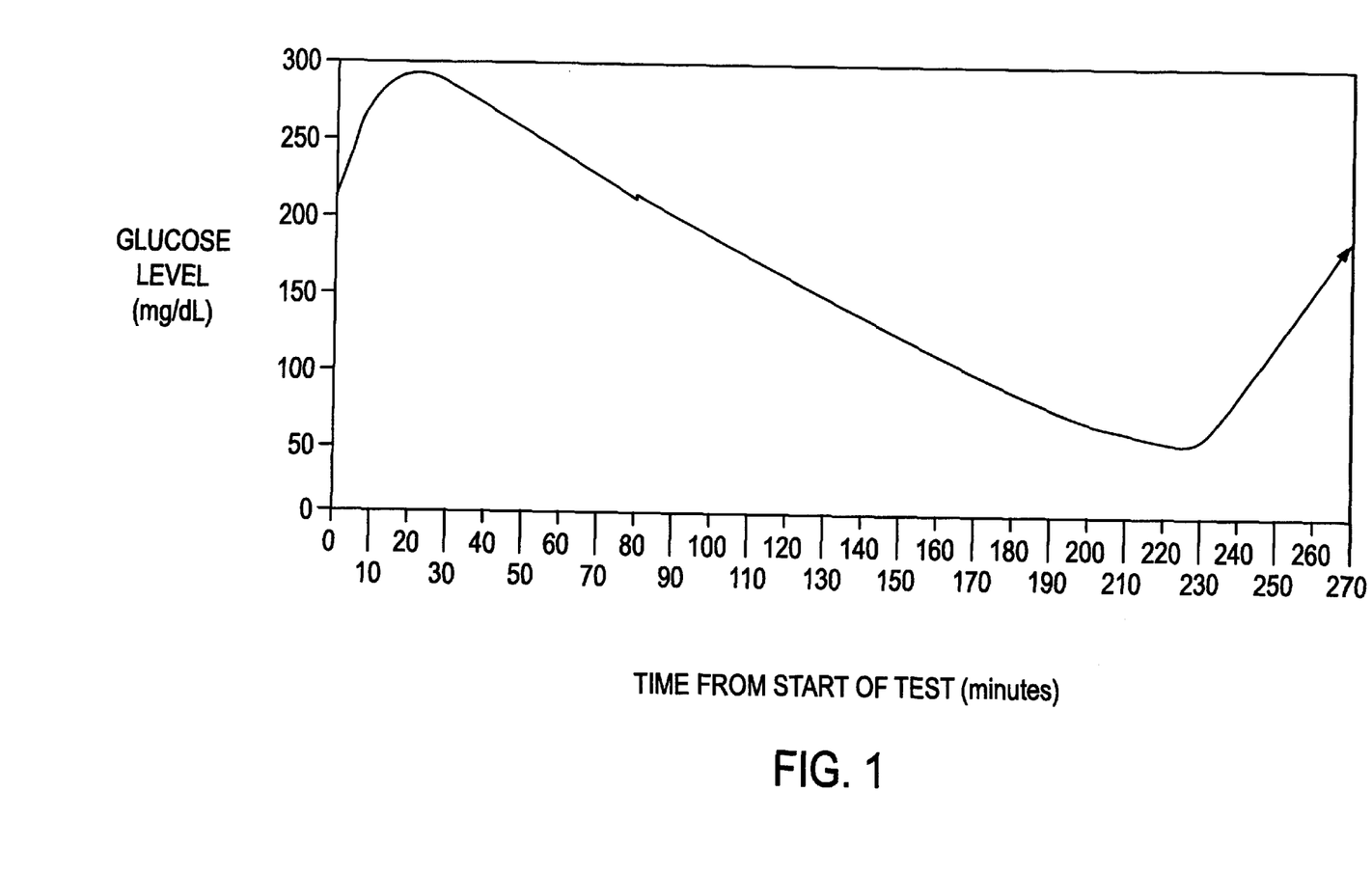
FIG. 1 shows a graph of a typical blood glucose concentration over a period of time.

FIG. 1 is a graph of blood glucose levels in a bloodstream measured over a period of 270 minutes. The graph shows a peak blood glucose level occurring at approximately 20 minutes after the start of measurement. The early peak is representative of a bolus of dextrose given to some of the test subjects at the start of the test in order to drive their blood glucose to rather high levels. The blood glucose level thereafter decreases at a substantially steady rate until a time of approximately 220 minutes. The decreasing portion of the graph represents the absorption of blood glucose into the bloodstream from the digestive tract, and shows the decrease of blood glucose levels as the blood glucose is consumed by the body. The test subjects were given insulin at varied times during the decreasing blood glucose period. At a time of approximately 220 minutes, the graph shows an increase of blood glucose levels due to a consumption of a meal. A meal is defined as an intake of nutrients that causes a rise in a blood analyte, such as glucose, of at least 50 mg/dL in two hours. The blood glucose level increases at a substantially steady rate following the meal. The graph represents a typical blood glucose response, and is not the response of any particular person. The graph was constructed from tests performed at the National Institutes of Health (NIH) Clinical Center on ten test subjects having diabetes. The test data shows typical trends in blood glucose levels before and after a meal. This predictable and substantially constant blood glucose response can be used as an aid in predicting and measuring blood glucose levels with a non-invasive quantitative measurement instrument. The graph shows that the rate of decrease of blood glucose level is about one half the rate of increase of blood glucose level.

Figure 2:
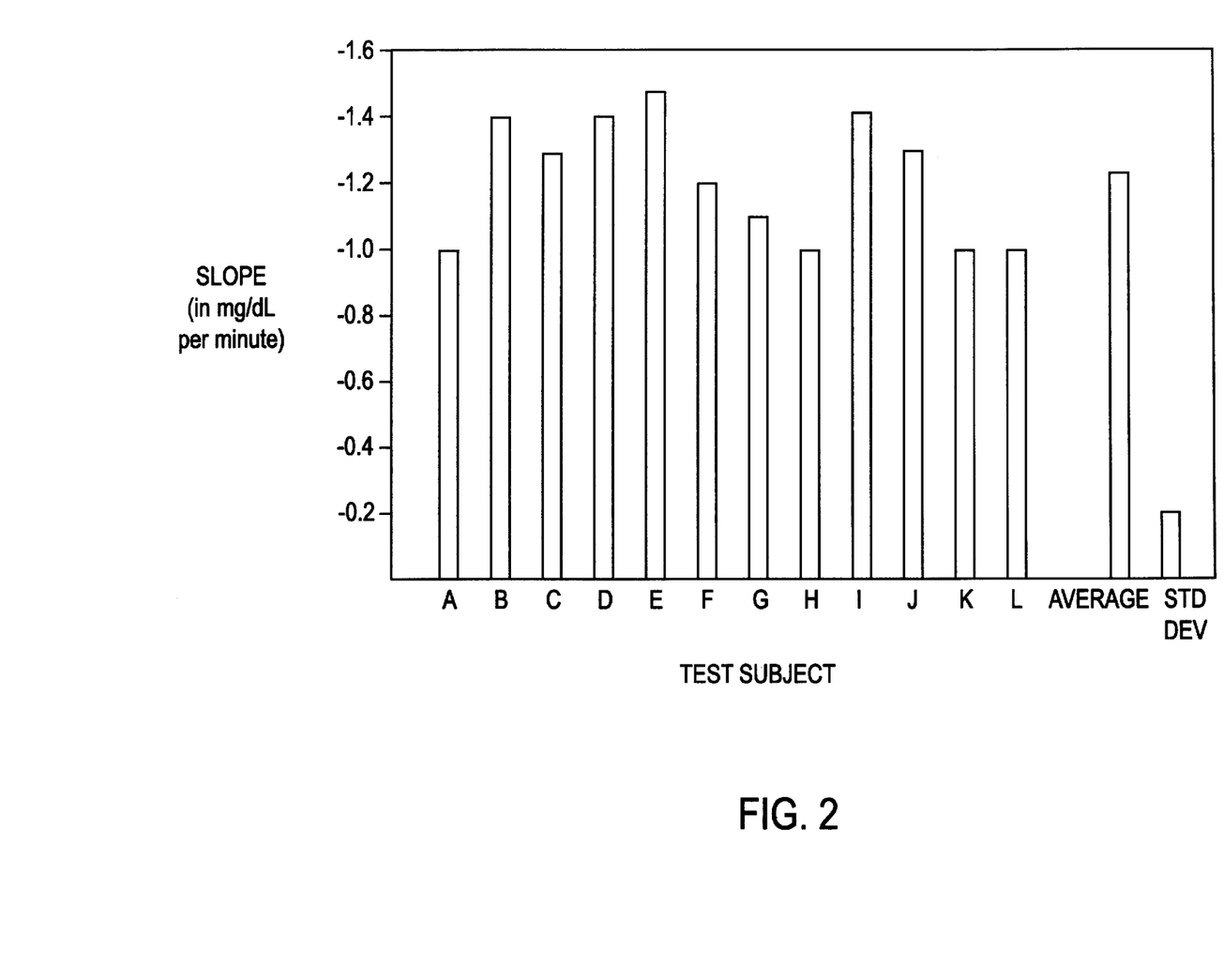
FIG. 2 shows the blood glucose fall rate measured in test subjects.

FIG. 2 is a bar graph of the decreasing blood glucose trends after a peak has occurred. The data was collected using twelve test subjects, labeled A through L. Ten of the twelve test subjects were the ten test subjects from the NIH depicted in the previous graph. The graph shows an average slope of a negative 1.2 mg/dL per minute for the decreasing portion of blood glucose levels. The data in the graph represents the decreasing blood glucose levels period in the graph of FIG. 1, from approximately 20 minutes to approximately 220 minutes.

Figure 3:
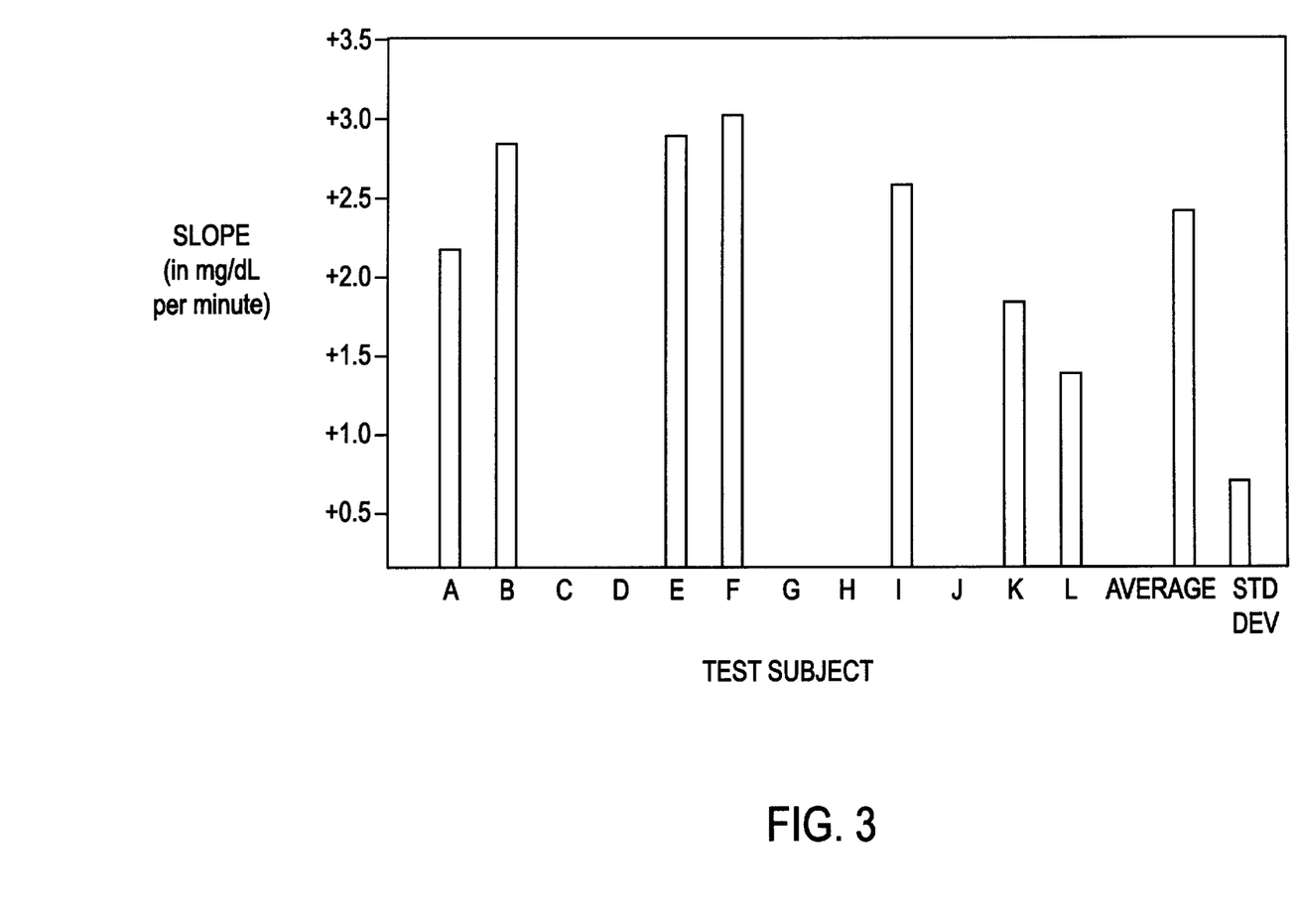
FIG. 3 shows the blood glucose rise rate measured in test subjects.

FIG. 3 is a bar graph of the increasing blood glucose trends after a meal was ingested. The data was collected using seven of the twelve test subjects used in the above graph. The graph shows an average slope of a positive 2.4 mg/dL per minute for the increasing portion of the graph, from approximately 220 minutes to approximately 270 minutes.

Figure 4:
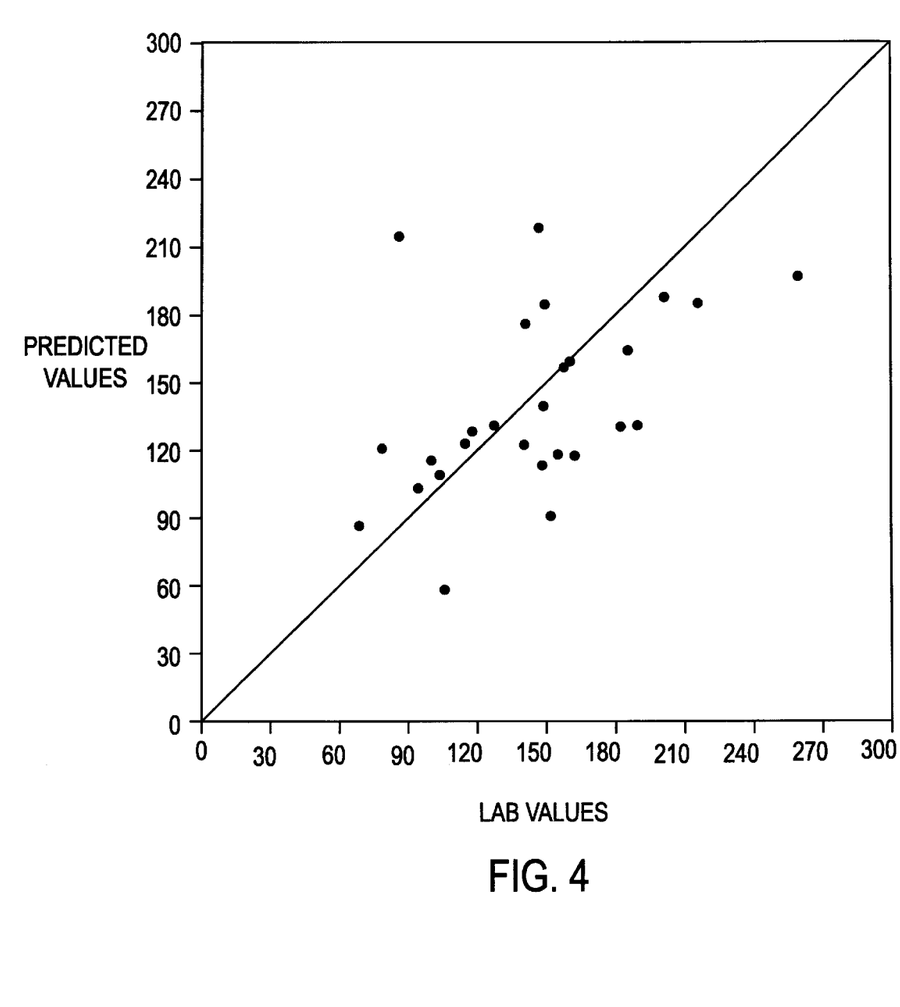
FIG. 4 shows a comparison of an un-aided near-infrared instrument to a laboratory measurement.

FIG. 4 is a graph representing the accuracy of a low precision un-aided quantitative measurement instrument, such as a non-invasive near-infrared instrument of the prior art using lower precision sensors. By un-aided, it is meant that the instrument does not employ the method of the present invention in order to improve accuracy. The graph depicts the predicted values of such an un-aided near-infrared instrument on the vertical axis versus laboratory blood glucose measurements from blood samples on the horizontal axis. The laboratory blood glucose measurements are used as an accuracy standard. The purpose of the graph is an accuracy comparison, where a perfect agreement between the two types of measurements would fall on the diagonal line of the graph. The graph shows a correlation of 0.462 between the un-aided measurement instrument and the laboratory measurements from blood samples. This is not a satisfactory accuracy level for blood analyte measurement.

A typical prior art near-infrared quantitative measurement instrument produces a measurement by employing a regression analysis equation to arrive at a predicted value in mg/dL. The regression analysis equation is typically of the form:

$$\text{mg/dL} = C_0 + C_1 * OD_1 + \ldots + C_n * OD_n + C_{n+1} * T_{SYSTEM} + C_{n+2} * T_{DETECTOR} + C_{n+3} * T_{BODY}. \quad (1)$$

In equation (1), the C values $C_0$ through $C_{n+3}$ are calibration constants. The OD values $OD_1$ through $OD_n$ are given by Log $1/I_n$ at the various wavelengths, where $I_n$ is equal to the period of the near-infrared light as determined by the wavelength "n" employed by the instrument. Multiple wavelengths of light "n" may be used in performing a measurement of optical energy absorbed by the body part under test. $T_{SYSTEM}$ is the temperature of the optical illumination system, $T_{DETECTOR}$ is the temperature of the optical detector, and $T_{BODY}$ is the temperature of the body part being used for the blood glucose measurement, one or more of which may be omitted from the equation.

A typical prior art near-infrared quantitative measurement instrument generates a predicted blood glucose measurement value by directing optical energy through a body part, typically a finger. A receiver captures the optical energy that successfully passes through the body part, with the receiver being capable of measuring the received optical energy. The instrument also measures the temperatures of the optical illumination system ($T_{SYSTEM}$), the optical detector ($T_{DETECTOR}$), and the body part ($T_{BODY}$). The instrument calculates the OD values for all of the optical wavelengths employed by the instrument. The regression analysis equation (1) is then multiplied out using the above terms to give the predicted value of the blood glucose level.

Equation (1) requires that the measurement system be extremely stable in order to measure the very low concentration of glucose that is present in the bloodstream. To successfully use equation (1) requires a measurement system with Log1/I repeatability errors of less than 0.001. To achieve such precision, when measuring a human subject, requires a very precise optical instrument.

Figure 5:
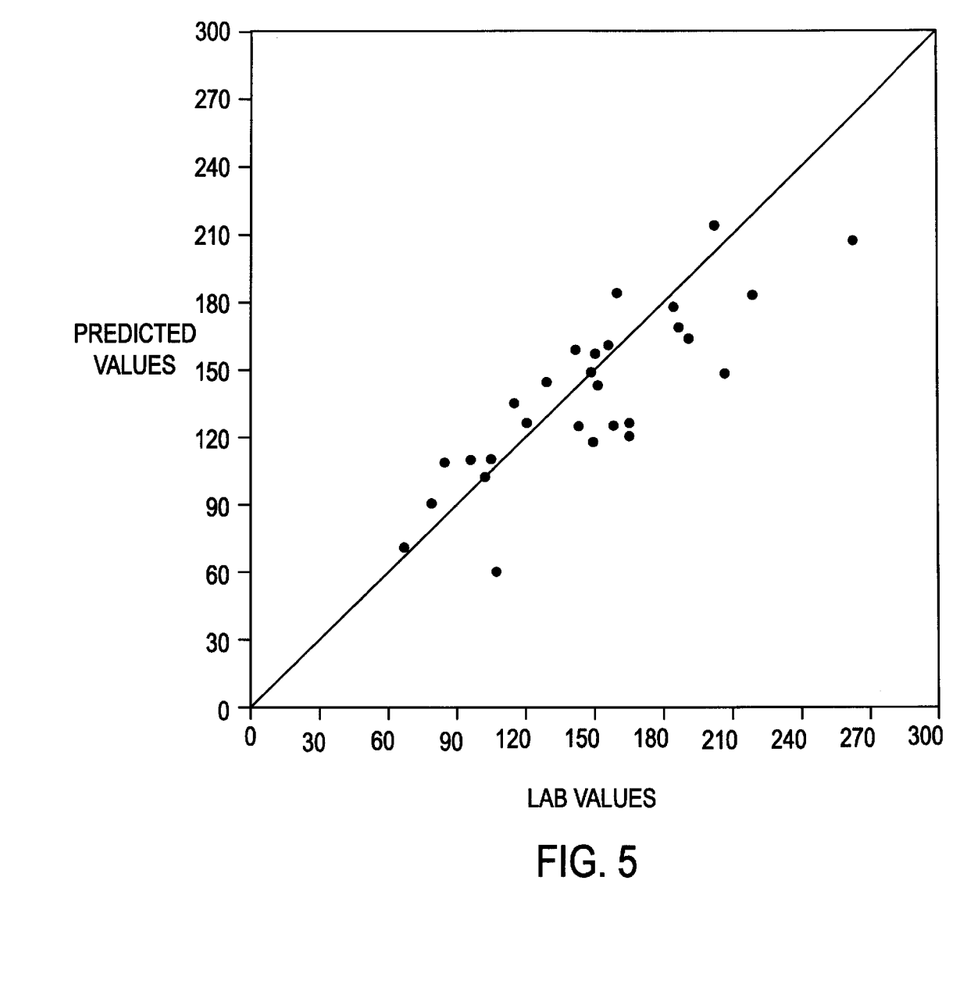
FIG. 5 shows a comparison of a near-infrared instrument aided by a first embodiment of the present invention to a laboratory measurement.

FIG. 5 is a graph representing the accuracy of a quantitative measurement instrument employing a first embodiment of the present invention. To improve the accuracy of an instrument with less precise optics, the a priori knowledge that blood glucose increases for about two hours after meals, at a rate that is approximately twice the rate that it decreases through the administration of medication, allows an additional regression term to be included with the previously described equation. The graph depicts the predicted values of the first embodiment on the vertical axis versus the laboratory blood glucose measurements from blood samples on the horizontal axis. The graph shows a correlation of 0.832 between the first embodiment and laboratory measurements. This is of a sufficient level of accuracy to allow the use of simpler, less precise optics in the measurement instrument. In addition, a segmental calibration technique can be employed in conjunction with the present invention to provide optimal accuracy of the instrument. The segmental calibration technique is described in detail in U.S. Pat. No. 5,068,536 to Rosenthal, the disclosure of which is incorporated herein by reference.

The present invention also uses a regression analysis equation to produce a predicted value, with the addition of a $C_{n+4}*J$ term to the regression analysis equation, where:

$$J=(2-t_{LM})/A \qquad (2)$$

This J term equation (2) is based on the knowledge that the peak blood glucose value for an individual occurs at a reasonably constant time (e.g. approximately two hours) after a meal. The J term equation (2) assumes that the rise rate of blood glucose is twice as high as the fall rate. Here tLM is the number of hours since the last meal. The A term is one of two values; a positive two if $(2-t_{LM})$ is a positive number, or a negative one if $(2-t_{LM})$ is a negative number.

In the method of the first embodiment, the quantitative measurement instrument generates a predicted blood glucose measurement value by directing a form of energy through a body part, typically a finger. In a preferred embodiment, the energy is near-infrared optical energy, although a person skilled in the art will recognize that other types of energy, such as radio-frequency energy, may also be used to perform the measurement. A receiver captures the optical energy that successfully passes through the body part, with the receiver being capable of measuring the received optical energy. The instrument also measures the temperatures of the optical illumination system ($T_{SYSTEM}$), the optical detector ($T_{DETECTOR}$), and the body part ($T_{BODY}$). As discussed above, one or more of these temperature measurements may be omitted. The instrument calculates the OD values for all of the optical wavelengths employed by the instrument, and inserts the variables in the J term equation (2) to complete the regression analysis equation. The regression analysis equation (1) is then multiplied out using the J term equation (2) to give the predicted value of blood glucose concentration.

Two limitations exist with this approach. The first limitation is the possible inaccuracy if a measurement is performed following an overnight fast, such as prior to breakfast. Then a factor of about 1.6 should be used in place of the calculated J term equation (2). The second limitation is the possible inaccuracy if a measurement is performed an extended time after a meal, such as more than about six hours after a meal. For this case the result of the J term equation (2) is limited to a maximum of about four.

Figure 6:
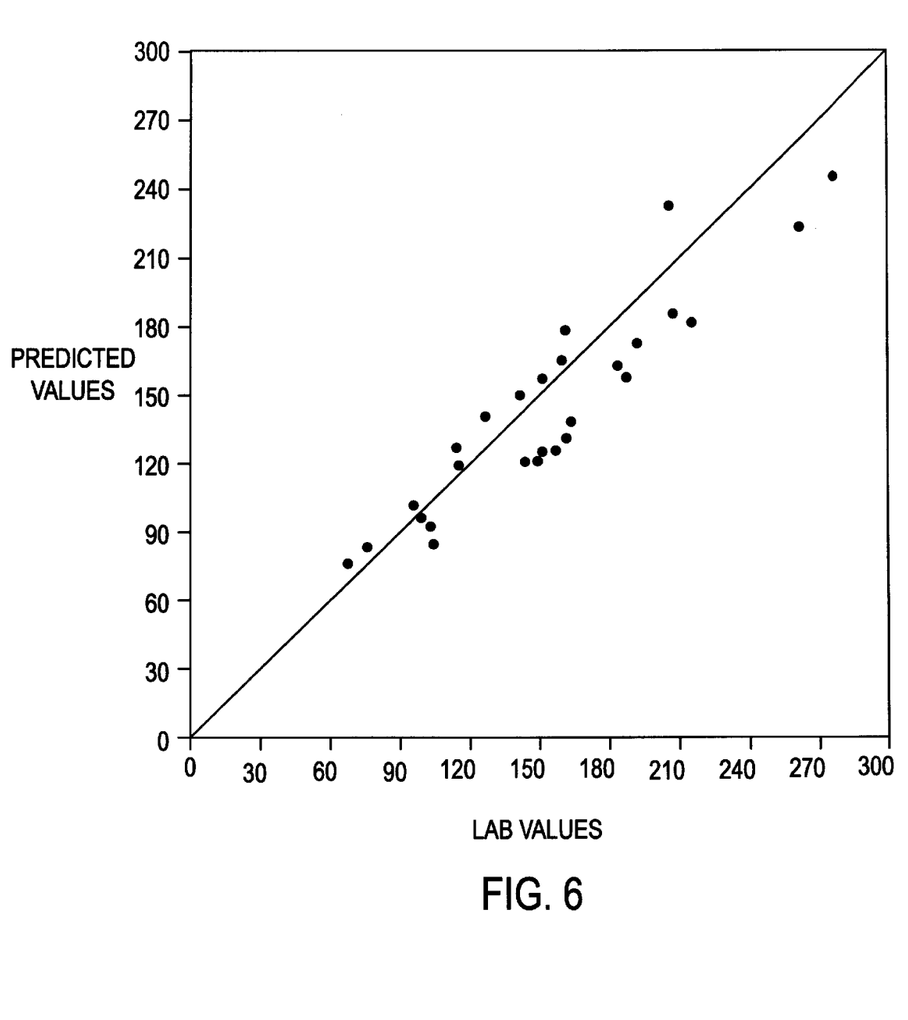
FIG. 6 shows a comparison of a near-infrared instrument aided by a second embodiment of the present invention to a laboratory measurement.

FIG. 6 is a graph representing the accuracy of a quantitative measurement instrument employing a second embodiment of the present invention. The graph depicts the predicted values of the second embodiment on the vertical axis versus the laboratory blood glucose measurements from blood samples on the horizontal axis. The graph shows a correlation of 0.936 between the second embodiment and laboratory measurements. This high level of accuracy allows the use of simpler, less precise optics in the instrument.

In a second embodiment, the measurement instrument uses indicator variable math in a regression analysis equation to obtain a predicted blood glucose value in mg/dL, where:

$$mg/dL = K_0 + K_1*OD_1 + \ldots + K_{14}*OD_{14} + K_{15}*X_0 + K_{16}*X_1 + K_{17}*X_2 + K_{18}*X_3 + K_{19}*X_4 + K_{20}*X_5 + K_{21}*X_6 + K_{22}*X_7 + K_{23}*X_8. \qquad (3)$$

In equation (3) the K values $K_0$ through $K_{23}$ are calibration constants, and one or more of the above temperature measurements also may be included. Fourteen wavelengths are given as an example, but more or less than fourteen may be employed. The OD values $OD_1$ through $OD_{14}$ are given by Log $1/I_n$ at the various wavelengths. Multiple wavelengths of light may be used in performing a measurement of optical energy absorbed by the body part under test. The variables $X_0$ through $X_8$ are the indicator groups derived from the time of the last meal. The indicator $X_0$ is given a value of one if the measurement was taken prior to a breakfast meal (i.e., after an overnight fast), and a value of zero otherwise. The indicator $X_1$ is given a value of one if the measurement was taken in a period of zero to one half hours after a meal, and a value of zero otherwise. The indicators $X_2$ and $X_3$ are given a collective value of one if the measurement was taken in a period between one half to one and a half hours after a meal, and are both given a value of zero otherwise. The division of the collective value between the two indicators will be determined via linear interpolation. The interpolation divides the collective value of one between the two indicators according to where the elapsed time since the last meal falls within the time range of the two indicator variables. For example, if a measurement was performed at 1.1 hours after a meal, a value of 0.40 will be entered into $X_2$ and 0.60 into $X_3$. The indicators $X_3$ and $X_4$ are given a collective value of one if the measurement was taken in a period between one and a half to two and a half hours after a meal, and are both given a value of zero otherwise. The indicators $X_4$ and $X_5$ are given a collective value of one if the measurement was taken in a period between two and a half to three and a half hours after a meal, and are both given a value of zero otherwise. The indicators $X_5$ and $X_6$ are given a collective value of one if the measurement was taken in a period between three and a half to four and a half hours after a meal, and are both given a value of zero otherwise. The indicators $X_6$ and $X_7$ are given a collective value of one if the measurement was taken in a period between four and a half to five and a half hours after a meal, and are both given a value of zero otherwise. The indicators $X_7$ and $X_8$ are given a collective value of one if the measurement was taken in a period between five and a half to six and a half hours after a meal, and are both given a value of zero otherwise. The indicator $X_8$ is given a value of one if the measurement was taken more than six and a half hours after a meal, and is given a value of zero otherwise.

In the method of the second embodiment, the quantitative measurement instrument generates a predicted blood glucose measurement value by directing a form of energy through a body part, typically a finger. In a preferred embodiment, the energy is near-infrared optical energy, although a person skilled in the art will recognize that other types of energy, such as radio-frequency energy, may also be used to perform the measurement. The instrument measures the energy that passes through the body part. The OD values are calculated for all of the optical wavelengths employed by the instrument, and the time since the last meal is calculated. The indicators $X_0$ through $X_8$ are then calculated based on the time since the last meal, with interpolation used to calculate the values for the paired indicators. The regression analysis equation is then multiplied out using the above terms to give the predicted value of the blood glucose level.

To calibrate an instrument that uses the indicator variables method, a two-step calibration process may be used. First, a regression analysis is performed using the OD optical terms (e.g., Log $1/I_1$ through Log $1/I_{14}$). Second, the optical error is derived by predicting a blood glucose value for each calibration reading at a given wavelength by using the calibration constants derived from the calibrations, using only the optical terms. The predicted value for each sample is then subtracted from the laboratory-measured value of that sample. The result is the optical error corresponding to the laboratory sample. The optical errors for all of the calibration samples are placed into a file that becomes the dependent variable for a multiple linear regression analysis, while the independent variables are the nine indicator variables that have been previously described. The resulting calibration constants are then added to the calibration constants previously derived from the optical terms, and become the final calibration constants $K_0$ through $K_{23}$. Using this two-step approach allows the optical information to provide the maximum amount of predictive value.

In a third embodiment of the invention, the relative size of the meal is taken into account through a regression analysis equation employing meal indicator variables. This embodiment gives weight to a meal base on its size. The third embodiment employs dual calibration constants to weight the size of the meal, where:

$$mg/dL = K_0 + K_1{}^*OD_1 + \ldots + K_{14}{}^*OD_{14} + K_{15}{}^*M_{15}{}^*C_{15}{}^*R_{15} + K_{16}{}^*M_{16}{}^*C_{16}{}^*R_{16} + \ldots + K_{22}{}^*M_{22}{}^*C_{22}{}^*R_{22} + K_{23}{}^*T_{23} + K_{24}T_{24}. \quad (4)$$

In equation (4) the K values $K_0$ through $K_{23}$ again are calibration constants. The T terms are the previously defined temperature terms $T_{SYSTEM}$, $T_{DETECTOR}$, and $T_{BODY}$ combined into one. The OD values $OD_1$ through $OD_{14}$ are given by Log I at various wavelengths. The variable R is the relative caloric value of the meal. The constants $C_{15}$ through $C_{22}$ are calibration constants that are also dependent on the caloric value of the meal. The variables $M_{15}$ through $M_{22}$ are the meal indicator values similar to the indicator variables $X_0$ through $X_8$, with their values given as explained with reference to the second embodiment.

In operation, a person will enter a relative size of the last meal into the device (e.g., the size R would be a 1 for a very light meal and a 10 for an extremely heavy meal). The dual calibration constants K and C can then be solved by an iterative process. First, the terms containing the C values and the R values are held equal to 1 while calculating the optimum K values. Second, for the entered value of R and the produced K values a new set of C values are calculated using multiple linear regression. Third, the K values are recalculated while holding the values of C and R constant. This iteration process is continued until there is no more significant change in the C or K values.

Figure 7A:
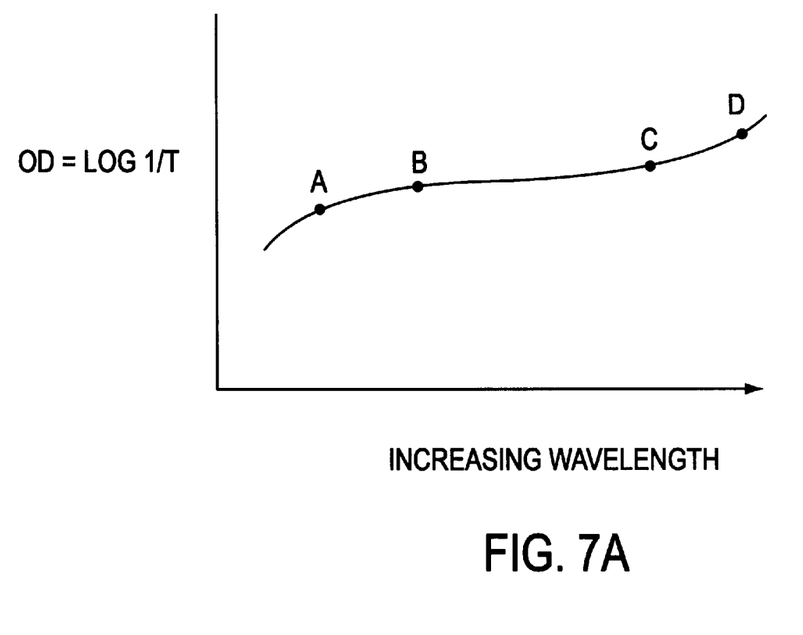
FIGS. 7A, 7B, and 7C are graphical representations of the division derivative math embodiment of the present invention.

A fourth embodiment of the present invention employs division derivative math to produce a predicted value of the blood glucose concentration. If the division derivative math is linearly related to the blood glucose concentration, then the previously described fourteen optical regression terms can be replaced by a single regression term. This is illustrated by FIG. 7A, where:

$$mg/dL = (d\ OD_1)/(d\ OD_2) = (d\ \text{Log}\ 1/T_1)/(d\ \text{Log}\ 1/T_2) == (\log 1/T_B - \text{Log}\ 1/T_A)/(\text{Log}\ 1/T_E - \text{Log}\ 1/T_D). \quad (5)$$

Figure 7B:
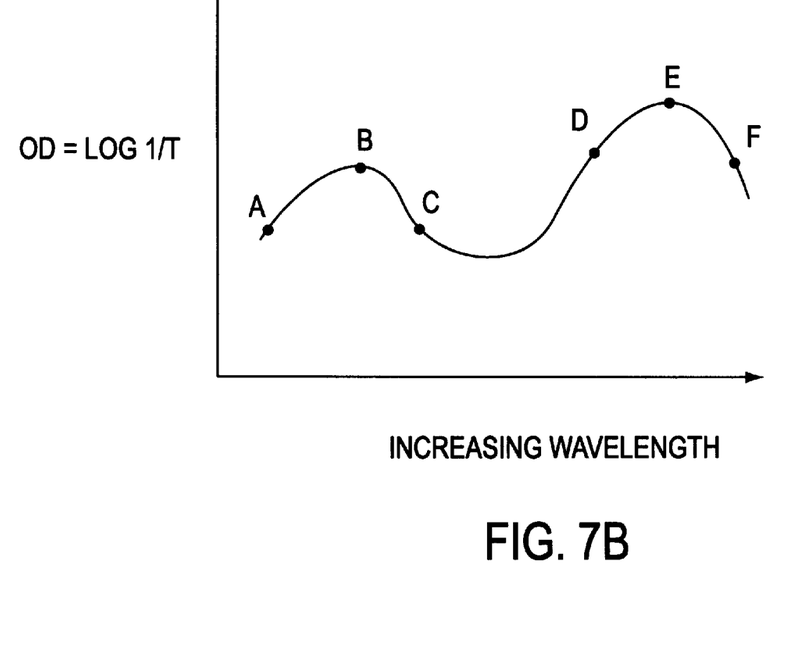

Similarly, a single term using second derivative math can be used. This is illustrated in FIG. 7B, where:

$$mg/dL = (d^2\ OD_1)/(d^2\ OD_2) = (d^2\text{Log}\ 1/T_1)/(d^2\ \text{Log}\ 1/T_2) == (\text{Log}\ 1/T_A - 2\text{Log}\ 1/T_B + \text{Log}\ 1/T_C)/(\text{Log}\ 1/T_D - 2\text{Log}\ 1/T_E + \text{Log}\ 1/T_F) \quad (5A)$$

The single regression term division derivative (4) above is suitable for a limited range of blood glucose concentrations, e.g., concentrations in the range of 40 to 120 mg/dL. Division derivative math allows accurate prediction of blood glucose concentrations even when significantly extrapolated outside the blood glucose calibration range.

Figure 7C:
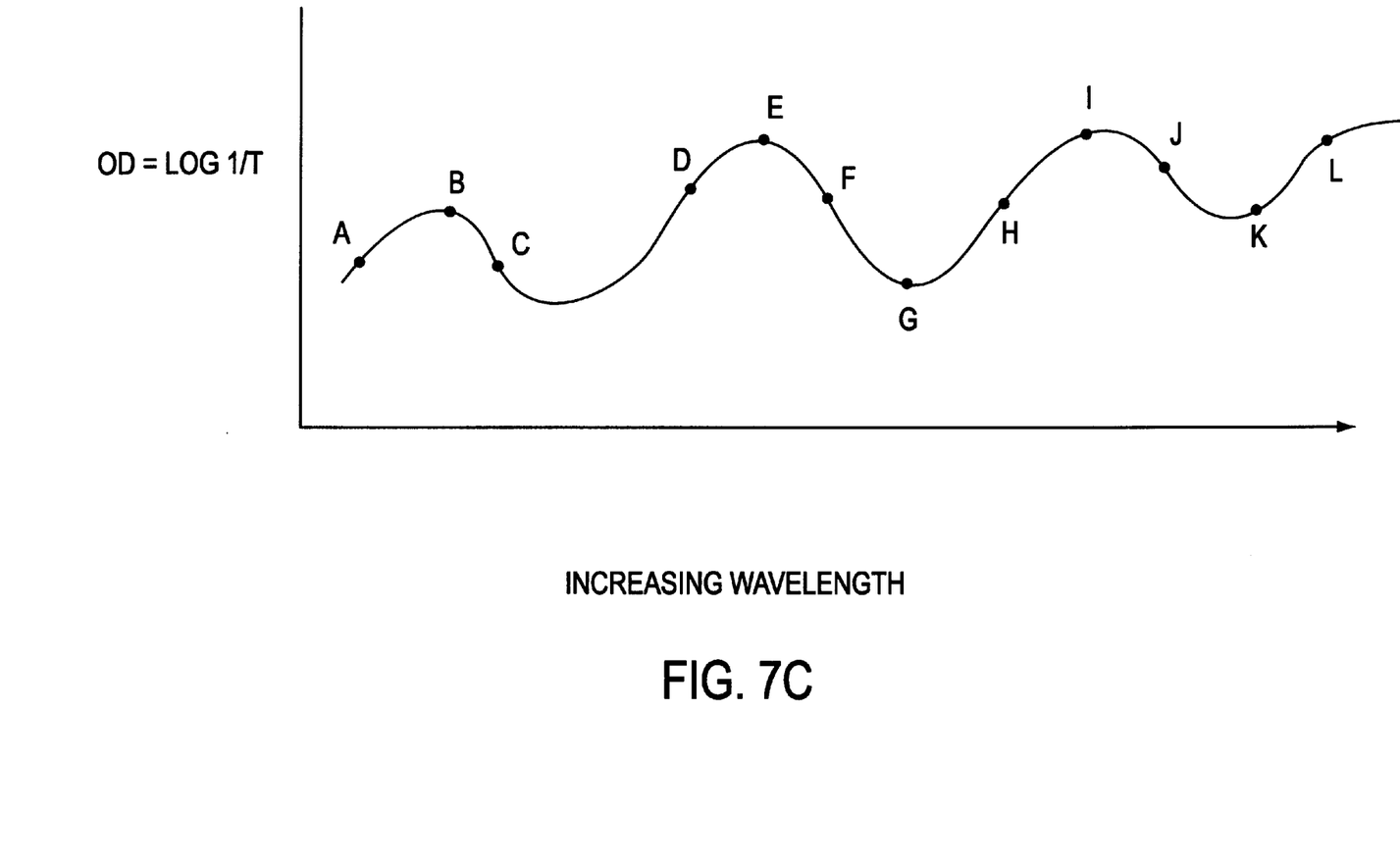

If the division derivative math is non-linearly related to blood glucose levels, then two term division derivative math must be used. These terms may be either first derivative or second derivative math. The second derivative two term division is illustrated in FIG. 7C where:

$$mg/dL = ((d^2OD_1)/(d^2OD_2)) + ((d^2OD_3)/(d^2OD_4)) == (d^2\ \text{Log}\ 1/T_i)/(d^2\ \text{Log}\ 1/T_2) + (d^2\ \text{Log}\ 1/T_3)/(d^2\ \text{Log}$$

$$1/T_4) = (\text{Log}\ 1/T_A - 2\text{Log}\ 1/T_B + \text{Log}\ 1/T_C)/(\text{Log}\ 1/T_D - 2\text{Log}\ 1/T_E + \text{Log}\ 1/T_F) + (\text{Log}\ 1/T_G - 2\text{Log}\ 1/T_H + \text{Log}\ 1/T_I)/(\text{Log}\ 1/T_J - 2$$

$$\text{Log}\ 1/T_K + \text{Log}\ 1/T_L). \quad (6)$$

The two regression term division derivative (6) above is suitable for an extended range of blood glucose concentrations, e.g. concentrations in the range of 40 to 400 mg/dL. The two regression term division derivative provides advantages similar to the single term division derivative math.

Figure 8:
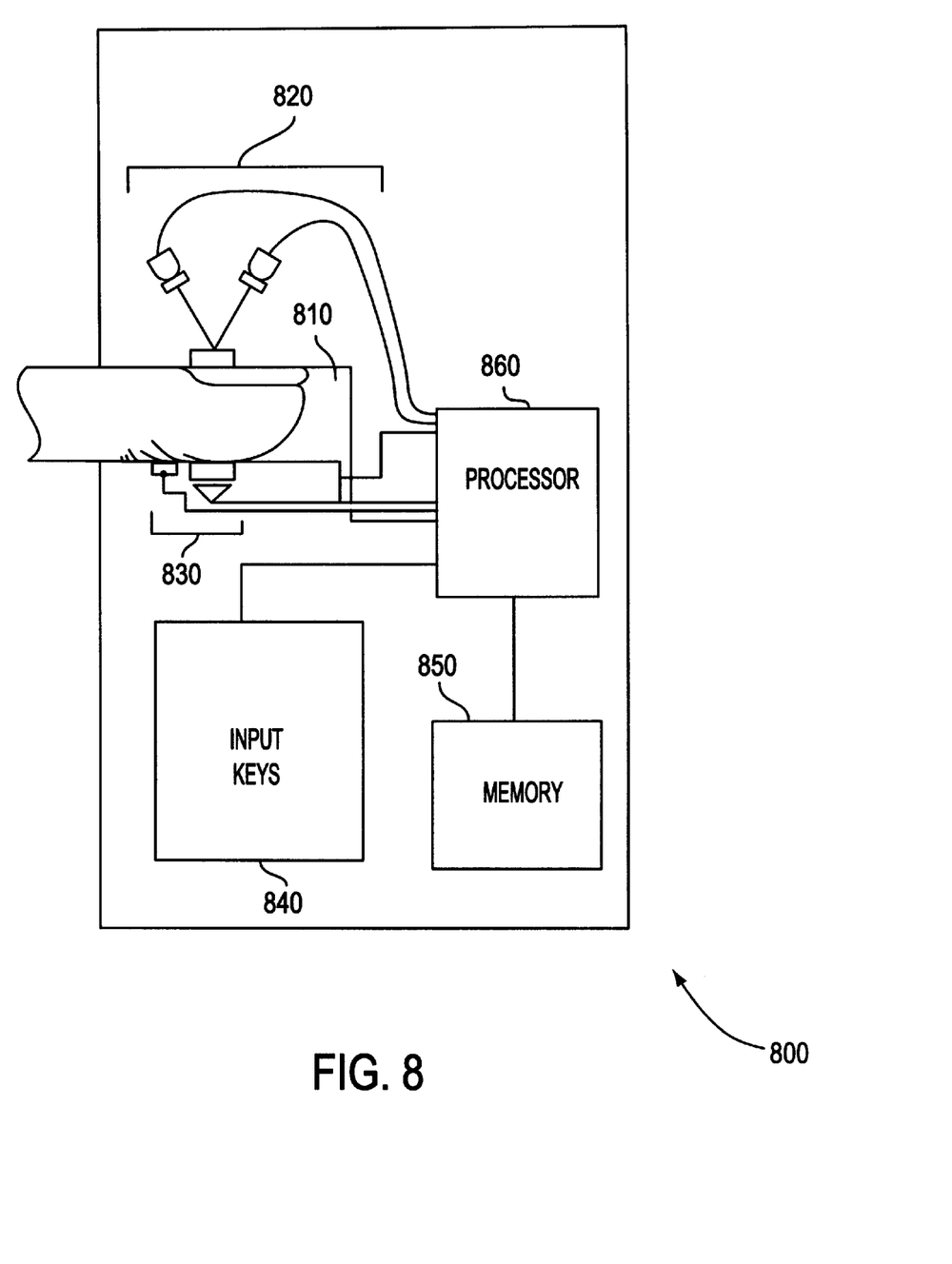
FIG. 8 shows an exemplary embodiment of a quantitative measurement instrument of the present invention.

FIG. 8 shows an exemplary embodiment of a quantitative measurement instrument 800 of the present invention having an improved accuracy characteristic. The quantitative measurement instrument 800 comprises an opening 810 for a body part, an introducing means 820 for introducing energy into the blood present in a body part of the subject, a detector circuit means 830 for detecting the energy emerging from the body part and producing an electrical signal indicative of the energy emerging from the body part, an input means 840 for entering the time since the last meal, a storage means 850 for storing the correction factor, and a processing means 860.

In operation, the subject inserts a body part into the opening 810, preferably a finger. The introducing means 820 directs energy through the body part. In the preferred embodiment, the energy comprises near-infrared energy, but alternatively the quantitative measurement instrument 800 may employ other sensor technologies. For example, the quantitative measurement instrument 800 may detect mid-infrared energy, far-infrared energy, or radio-frequency energy. The fundamental detection methodology would be the same as for the detection of near-infrared energy. The detector circuit means 830 receives the energy emerging from the body part and generates an electrical signal indicative of the quantity of emerging energy. The input means 840 is used to input the time since the last meal of the test subject. The processing means 860 receives the time since the last meal and uses it to create the correction factor, which is stored in the storage means 850. The processing means 860 also receives the electrical signal from the detector circuit means 830. The processing means 860 uses the regression equation, in conjunction with the correction factor, to yield a predicted value of the blood analyte concentration.

Figure 9:
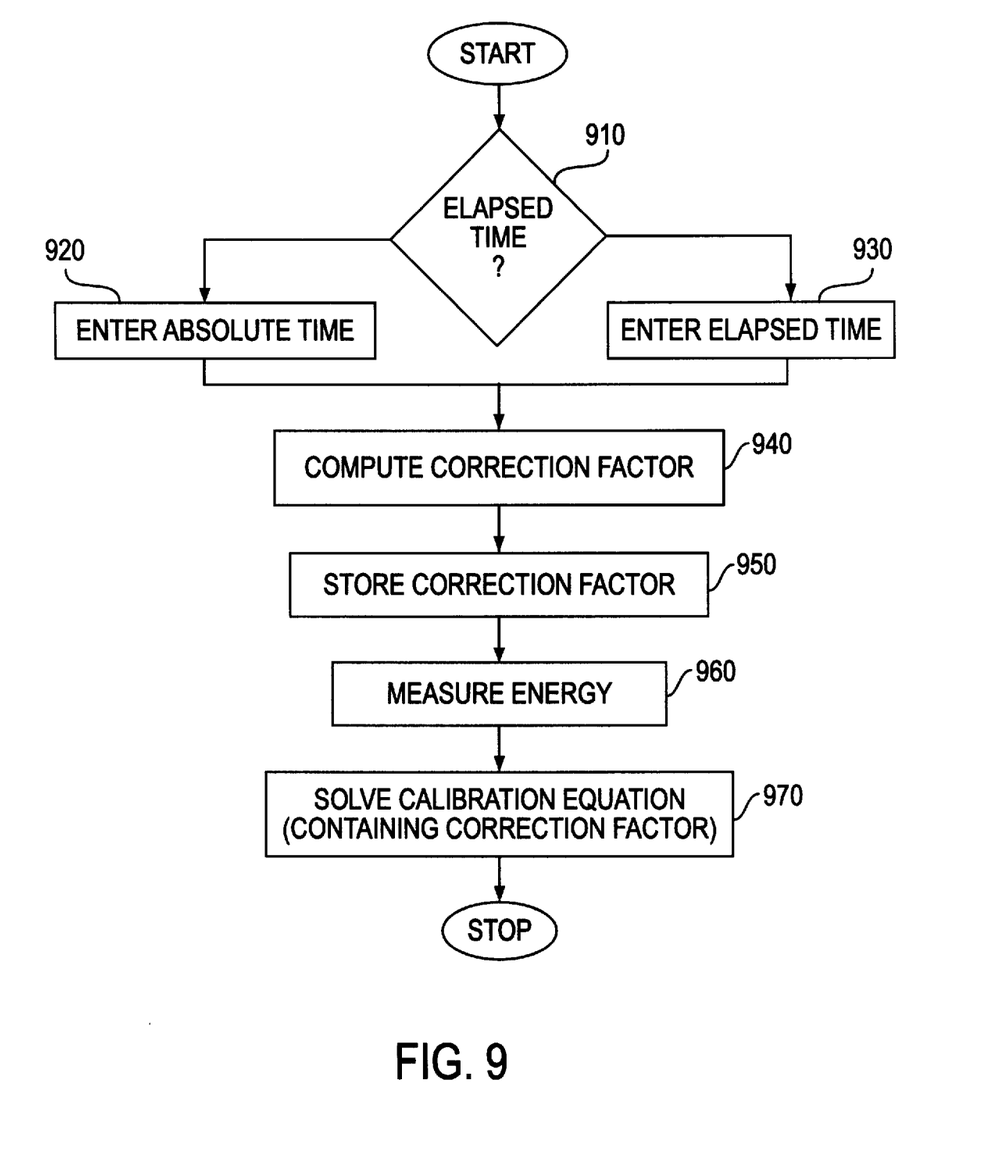
FIG. 9 shows a flowchart 900 illustrating the operation of the present invention.

FIG. 9 shows a flowchart 900 illustrating the operation of the present invention. In step 910 the quantitative measurement instrument 800 prompts the subject to enter the time since the last meal, entered via the input means 840. The subject can enter the time from the last meal in two ways. In step 920, the subject may enter the time as an absolute time (i.e., 12:00 pm), whereupon the processing means 860 computes the elapsed time from the last meal. Alternatively, in step 930, the subject may directly enter the elapsed time from the last meal. In step 940 the processing means 860 computes the correction factor using the elapsed time from the last meal. In step 950 the processing means 860 stores the computed correction factor in the storage means 850. In step 960 the quantitative measurement instrument 800 measures the energy emerging from the body part of the subject.

In step 970 the processing means 860 uses a calibration equation with constants that were derived from prior multiple regression analysis or other mathematical analysis factors (partial least squares, etc.), and generates a regression equation indicative of the energy emerging from the body part.

While the invention has been disclosed in detail above, the invention is not intended to be limited strictly to the invention as disclosed. It is evident that those skilled in the art may now make numerous uses and modifications of and departures from the specific embodiments described herein without departing from the inventive concepts.

What is claimed is:

1. A method for increasing an accuracy characteristic of a quantitative measurement instrument for measuring a blood analyte concentration, said method comprising:

obtaining an energy absorption measurement through a body part of an individual;

determining an elapsed time since a last intake of nutrients by said individual which results in an increase of said blood analyte of at least a minimum predetermined amount;

calculating a correction factor based on said elapsed time from said last intake of nutrients; and adding said correction factor to a regression analysis equation, wherein said regression analysis equation yields a predicted value of said blood analyte concentration.

2. The method of claim 1, wherein said blood analyte concentration is a blood glucose concentration.

3. The method of claim 1, wherein the step of obtaining said energy absorption measurement comprises the step of using a near-infrared optical absorption measurement.

4. The method of claim 1, wherein the step of obtaining said energy absorption measurement comprises the step of using a mid-infrared optical absorption measurement.

5. The method of claim 1, wherein the step of obtaining said energy absorption measurement comprises the step of using a far-infrared optical absorption measurement.

6. The method of claim 1, wherein the step of obtaining said energy absorption measurement comprises the step of using a radio-frequency absorption measurement.

7. The method of claim 1, wherein said correction factor has a rate of change represented by a multiplier of about positive two for a time period extending from said meal until about two hours after said meal.

8. The method of claim 1, wherein said correction factor has a rate of change represented by a multiplier of about negative one for a time period extending from about two hours after said meal onward.

9. The method of claim 1, wherein said correction factor is set at about one and sixth tenths if a measurement is a first measurement following an overnight fast.

10. The method of claim 1, wherein said correction factor is limited to a maximum value of about four for measurements made greater than about six hours after said meal.

11. A method for increasing an accuracy characteristic of a quantitative measurement instrument for measuring a blood analyte concentration, said method comprising:

obtaining an energy absorption measurement through a body part of an individual;

determining an elapsed time since a last meal; and allocating a plurality of indicator variables to form a regression analysis equation based on said elapsed time since said last meal, wherein said regression analysis equation yields a predicted value of said blood analyte concentration.

12. The method of claim 11, wherein said blood analyte concentration is a blood glucose concentration.

13. The method of claim 11, wherein the step of obtaining said energy absorption measurement comprises the step of using a near-infrared optical absorption measurement.

14. The method of claim 11, wherein the step of obtaining said energy absorption measurement comprises the step of using a mid-infrared optical absorption measurement.

15. The method of claim 11, wherein the step of obtaining said energy absorption measurement comprises the step of using a far-infrared optical absorption measurement.

16. The method of claim 11, wherein the step of obtaining said energy absorption measurement comprises the step of using a radio-frequency absorption measurement.

17. The method of claim 11, wherein a first indicator variable is assigned a value of one if said energy absorption measurement is obtained after a period of fasting, said first indicator variable is assigned a value of zero otherwise.

18. The method of claim 17, wherein a second indicator variable is assigned a value of one if said energy absorption measurement is obtained within about one half hour of said meal, said second indicator variable is assigned a value of zero otherwise.

19. The method of claim 18, wherein third and fourth indicator variables are assigned a collective value of one if said energy absorption measurement is obtained between about one half and about one and a half hours after said meal, with a division of said collective value between said third and fourth indicator variables being determined by linear interpolation, said third and fourth indicator variables are assigned a value of zero otherwise.

20. The method of claim 19, wherein said fourth indicator variable and a fifth indicator variable are assigned a collective value of one if said energy absorption measurement is obtained between about one and a half and about two and a half hours after said meal, with a division of said collective value between said fourth and fifth indicator variables being determined by linear interpolation, said fourth and fifth indicator variables are assigned a value of zero otherwise.

21. The method of claim 20, wherein said fifth indicator variable and a sixth indicator variable are assigned a collective value of one if said energy absorption measurement is obtained between about two and a half and about three and a half hours after said meal, with a division of said collective value between said fifth and sixth indicator variables being determined by linear interpolation, said fifth and sixth indicator variables are assigned a value of zero otherwise.

22. The method of claim 21, wherein said sixth indicator variable and a seventh indicator variable are assigned a collective value of one if said energy absorption measurement is obtained between about three and a half and about four and a half hours after said meal, with a division of said collective value between said sixth and seventh indicator variables being determined by linear interpolation, said sixth and seventh indicator variables are assigned a value of zero otherwise.

23. The method of claim 22, wherein said seventh indicator variable and a eighth indicator variable are assigned a collective value of one if said energy absorption measurement is obtained between about four and a half and about five and a half hours after said meal, with a division of said collective value between said seventh and eighth indicator variables being determined by linear interpolation, said seventh and eighth indicator variables are assigned a value of zero otherwise.

24. The method of claim 23, wherein said eighth indicator variable and a ninth indicator variable are assigned a collective value of one if said energy absorption measurement is obtained between about five and a half and about six and a half hours after said meal, with a division of said collective value between said eighth and ninth indicator variables being determined by linear interpolation, said eighth and ninth indicator variables are assigned a value of zero otherwise.

25. The method of claim 24, wherein said ninth indicator variable is assigned a value of one if said energy absorption measurement is obtained after about six and a half hours after said meal, said ninth indicator variable is assigned a value of zero otherwise.

26. A quantitative measurement instrument for non-invasive measurement of a blood analyte concentration, comprising:

introducing means including an energy source for introducing energy into blood present in a body part of a subject;

detector circuit means for detecting said energy emerging from said body part, said detector circuit means producing a first electrical signal indicative of said energy emerging from said body part;

input means for entering a time from a last intake of nutrients by said subject;

storage means for storing a regression equation and a correction factor, said correction factor having a value dependent on said entered time from a last intake of nutrients; and processing means for processing said first electrical signal by using said regression equation and said correction factor to yield a predicted value of said blood analyte concentration, with said correction factor increasing an accuracy characteristic of said quantitative measurement instrument, by taking into account the elapsed time of said last intake of nutrients in said regression equation.

27. The quantitative measurement instrument of claim 26, wherein said blood analyte concentration is a blood glucose concentration.

28. The quantitative measurement instrument of claim 26, wherein said energy comprises near-infrared energy.

29. The method of claim 26, wherein said energy comprises mid-infrared energy.

30. The method of claim 26, wherein said energy comprises far-infrared energy.

31. The quantitative measurement instrument of claim 26, wherein said energy comprises a radio-frequency energy.

32. A method for increasing an accuracy characteristic of a quantitative measurement instrument which utilizes a regression analysis equation for measuring a blood analyte concentration, said method comprising:

obtaining an energy absorption measurement through a body part of an individual;

determining an elapsed time since a last intake of nutrients by said individual which results in an increase of said blood analyte of at least a minimum predetermined amount; and modifying said regression analysis equation as a function of said elapsed time so as to obtain a blood analyte concentration measurement having increased accuracy by taking into account said last intake of nutrients.

\* \* \* \* \*